(12) United States Patent
Wodlinger et al.

(10) Patent No.: US 10,506,948 B2
(45) Date of Patent: Dec. 17, 2019

(54) LOCALIZATION FOR ELECTROCARDIOGRAPHIC MAPPING

(75) Inventors: Harold Wodlinger, Thornhill (CA); Charulatha Ramanathan, Solon, OH (US); Ping Jia, Solon, OH (US)

(73) Assignee: CARDIOINSIGHT TECHNOLOGIES, INC., Cleveland, OH (US)

( * ) Notice: Subject to any disclaimer, the term of this patent is extended or adjusted under 35 U.S.C. 154(b) by 1313 days.

(21) Appl. No.: 14/127,136

(22) PCT Filed: Jul. 5, 2012

(86) PCT No.: PCT/US2012/045582
§ 371 (c)(1),
(2), (4) Date: Apr. 30, 2014

(87) PCT Pub. No.: WO2013/006713
PCT Pub. Date: Jan. 10, 2013

(65) Prior Publication Data
US 2014/0235989 A1     Aug. 21, 2014

Related U.S. Application Data

(60) Provisional application No. 61/504,547, filed on Jul. 5, 2011.

(51) Int. Cl.
*A61B 5/06*     (2006.01)
*A61B 5/042*    (2006.01)
(Continued)

(52) U.S. Cl.
CPC .............. *A61B 5/063* (2013.01); *A61B 5/042* (2013.01); *A61B 5/066* (2013.01);
(Continued)

(58) Field of Classification Search
CPC ..... A61B 5/063; A61B 34/20; A61B 18/1492; A61B 5/042; A61B 5/066;
(Continued)

(56) References Cited

U.S. PATENT DOCUMENTS

| 5,553,611 A | 9/1996 | Budd et al. |
| 5,662,108 A | 9/1997 | Budd et al. |

(Continued)

FOREIGN PATENT DOCUMENTS

| EP | 1 023 870 A1 | 8/2000 |
| EP | 1 190 671 B1 | 12/2006 |

(Continued)

OTHER PUBLICATIONS

Int'l Search Report—3pgs., dated Jan. 10, 2013, CardioInsight Technologies, Inc.

(Continued)

*Primary Examiner* — Baisakhi Roy
*Assistant Examiner* — Patrick M Mehl
(74) *Attorney, Agent, or Firm* — Tarolli, Sundheim, Covell & Tummino LLP (57) ABSTRACT

A system (10) can localize an object in a patient's body. The system (10) can include a pulse generator (18 or 30) configured to provide a localization signal to at least one electrode that is fixed to the object in the patient's body. A sensor array (22) can be configured to detect an electrical field produced in response to the localization signal and provide respective sensor signals. A map generator (42) can be configured to reconstruct electrical signals based on the respective sensor signals and geometry data representing a geometric relationship between patient anatomy and the sensor array. A location calculator (50) can determine a location where the localization signal was applied based on the reconstructed electrical signals.

12 Claims, 7 Drawing Sheets

(51) Int. Cl.
*A61B 18/14* (2006.01)
*A61N 1/362* (2006.01)
*A61B 34/20* (2016.01)
*A61B 5/0402* (2006.01)
*A61B 5/00* (2006.01)

(52) U.S. Cl.
CPC .......... *A61B 18/1492* (2013.01); *A61B 34/20* (2016.02); *A61N 1/362* (2013.01); *A61B 5/0402* (2013.01); *A61B 5/4836* (2013.01); *A61B 2034/2053* (2016.02); *A61N 1/3625* (2013.01); *A61N 1/3628* (2013.01)

(58) Field of Classification Search
CPC . A61B 2034/2053; A61B 5/4836; A61B 5/06; A61B 18/14; A61B 5/00; A61N 1/362; A61N 1/3628; A61N 1/3625; A61N 1/0402
See application file for complete search history.

(56) References Cited

U.S. PATENT DOCUMENTS

| | | | |
|---|---|---|---|
| 5,697,377 | A | 12/1997 | Wittkampf |
| 5,713,946 | A | 2/1998 | Ben-Haim |
| 5,954,662 | A | 9/1999 | Swanson et al. |
| 6,115,630 | A | 9/2000 | Stadler et al. |
| 6,308,093 | B1 | 10/2001 | Armoundas et al. |
| 6,370,412 | B1* | 4/2002 | Armoundas ........... A61B 5/042 600/373 |
| 6,728,562 | B1 | 4/2004 | Budd et al. |
| 6,772,004 | B2* | 8/2004 | Rudy ................... A61B 5/0422 600/411 |
| 6,978,168 | B2 | 12/2005 | Beatty et al. |
| 7,146,214 | B2 | 12/2006 | Struble |
| 7,187,964 | B2 | 3/2007 | Khoury |
| 7,189,208 | B1 | 3/2007 | Beatty et al. |
| 7,263,397 | B2 | 8/2007 | Hauck et al. |
| 7,289,843 | B2 | 10/2007 | Beatty et al. |
| 7,505,810 | B2 | 3/2009 | Harlev et al. |
| 7,515,964 | B1 | 4/2009 | Harlev et al. |
| 2005/0101874 | A1 | 5/2005 | Beatty et al. |
| 2006/0173251 | A1 | 8/2006 | Govari et al. |
| 2007/0219452 | A1 | 9/2007 | Cohen et al. |
| 2009/0157136 | A1* | 6/2009 | Yang .................... A61B 5/0422 607/17 |
| 2011/0137151 | A1 | 6/2011 | Lichtenstein |
| 2011/0160574 | A1 | 6/2011 | Harlev et al. |

FOREIGN PATENT DOCUMENTS

| | | |
|---|---|---|
| GB | 2301037 A | 11/1996 |
| JP | 8-322950 | 12/1996 |
| JP | 2009-106633 | 5/2009 |
| WO | WO 2006/060426 A2 | 6/2006 |
| WO | WO 2007/137077 A3 | 11/2007 |
| WO | WO 2008 048780 A1 | 4/2008 |
| WO | WO 2005/053792 A1 | 6/2008 |
| WO | WO 2008/129510 A2 | 10/2008 |
| WO | WO 2008/136008 A2 | 11/2008 |
| WO | WO 2009/045852 A1 | 4/2009 |
| WO | WO 2010/019494 | 2/2010 |

OTHER PUBLICATIONS

Antonis A. Armoundas: "A Novel Technique for Guiding Ablative Therapy of Cardiac Arrhythmias"; Jun. 1, 1999, MIT, XP055167139.
Applicant: CardioInsight Technologies, Inc., Application No. 12807883.9; Supplementary European Search Report, search completed Feb. 5, 2015, 2 pp.
Office action for European Patent Application No. 12 807 883.9, dated Sep. 28, 2017.
Canadian Application No. 2841388; Owner: Cardioinsight Technologies, Inc.; Canadian Office Action dated March 22, 2018; 6 PGS.
Canadian Application No. 2841388; Owner: Cardioinsight Technologies, Inc.; Canadian Office Action dated Feb. 12, 2019; 5 PGS.

* cited by examiner

LOCALIZATION FOR ELECTROCARDIOGRAPHIC MAPPING

CROSS-REFERENCE TO RELATED APPLICATION

This application claims the benefit of U.S. Provisional Patent Application No. 61/504547, filed on Jul. 5, 2011 and entitled LOCALIZATION FOR ELECTROCARDIOGRAPHIC MAPPING, which is incorporated herein by reference in its entirety.

TECHNICAL FIELD

This disclosure relates to systems and methods for performing localization of an object, such as for electrocardiographic mapping.

BACKGROUND

Various procedures exist in which an object is inserted into a patient's body as part of a low invasive procedure in which a view of the object is obstructed from a direct line of sight. An example of such a procedure is an electrophysiology study in which a catheter is used for accessing a remotely located part of the human or animal body, such as via a vein or artery. For example, a catheter may be provided with one or more electrodes or other components disposed on a tip of the catheter. The one or more electrodes or other components can be configured to perform diagnostic (e.g., sensing) function and/or other functions (e.g., stimulation or ablation), for example. In such operations, it is desirable to determine a position of the catheter or other object, which is referred to as localization.

SUMMARY

This disclosure relates to systems and methods for performing localization of an object.

In some examples, a system can be provided to localize an object in a patient's body. The system can include a pulse generator configured to provide a localization signal to at least one electrode that is fixed to the object in the patient's body. A sensor array can be configured to detect an electrical field produced in response to the localization signal and provide respective sensor signals. A map generator can be configured to reconstruct electrical signals based on the respective sensor signals and geometry data representing a geometric relationship between patient anatomy and the sensor array. A location calculator can determine a location where the localization signal was applied based on the reconstructed electrical signals.

In other examples, a method can be performed for localizing an object. The method can include controlling a localization signal that is supplied to an electrode, associated with the object, to produce an electrical field in tissue of a patient. The method can also include storing sensed electrical data in memory based on sensing electrical signals corresponding to the electrical field and storing geometry data in the memory. The geometry data can represent a geometric relationship between patient anatomy and a plurality of sensors used to detect the electric field. The method can also include reconstructing electrical signals at an anatomical envelope for the tissue based on the geometry data and the sensed electrical signals. The reconstructed electrical signals can be analyzed to determine a location where the localization signal was applied. The method can be implemented as a computer-implemented method or it can be implemented as instructions executable stored in a readable medium, such as may be executed by a processor.

DETAILED DESCRIPTION

This disclosure relates to systems and methods for performing localization. The systems and methods disclosed herein can be employed to localize an object, such as a catheter or pacing lead, by applying a localization signal (e.g., a pulse) to a patient's tissue to produce an electric field. In some examples, the localization signal is applied as a subthreshold electrical signal pulse that has insufficient energy to stimulate adjacent tissue. In other examples, the localization signal can applied as a supra threshold electrical pulse designed to stimulate adjacent tissue (e.g., a pacing pulse). Electrical signals corresponding to the electrical field can be sensed via a plurality of sensors, such as an arrangement of body surface electrodes, having a position that is known relative to patient anatomy corresponding to geometry data. The sensed electrical signals can be mapped to tissue (e.g., corresponding to patient anatomy or a generic heart model) or other geometry based on geometry data for the patient. The geometry data provides (or can be used to derive) position information relating to patient anatomy and the plurality of sensors. A location where the localization signal was applied to the heart can be determined from the mapped electrical signals. The location can in turn be presented on a display to identify the location of the object relative to patient anatomy. While the examples disclosed herein relate to localization of an object with respect to a patient's heart, the approach disclosed herein is equally applicable to localize objects in other tissue such as the brain, for example.

Figure 1:
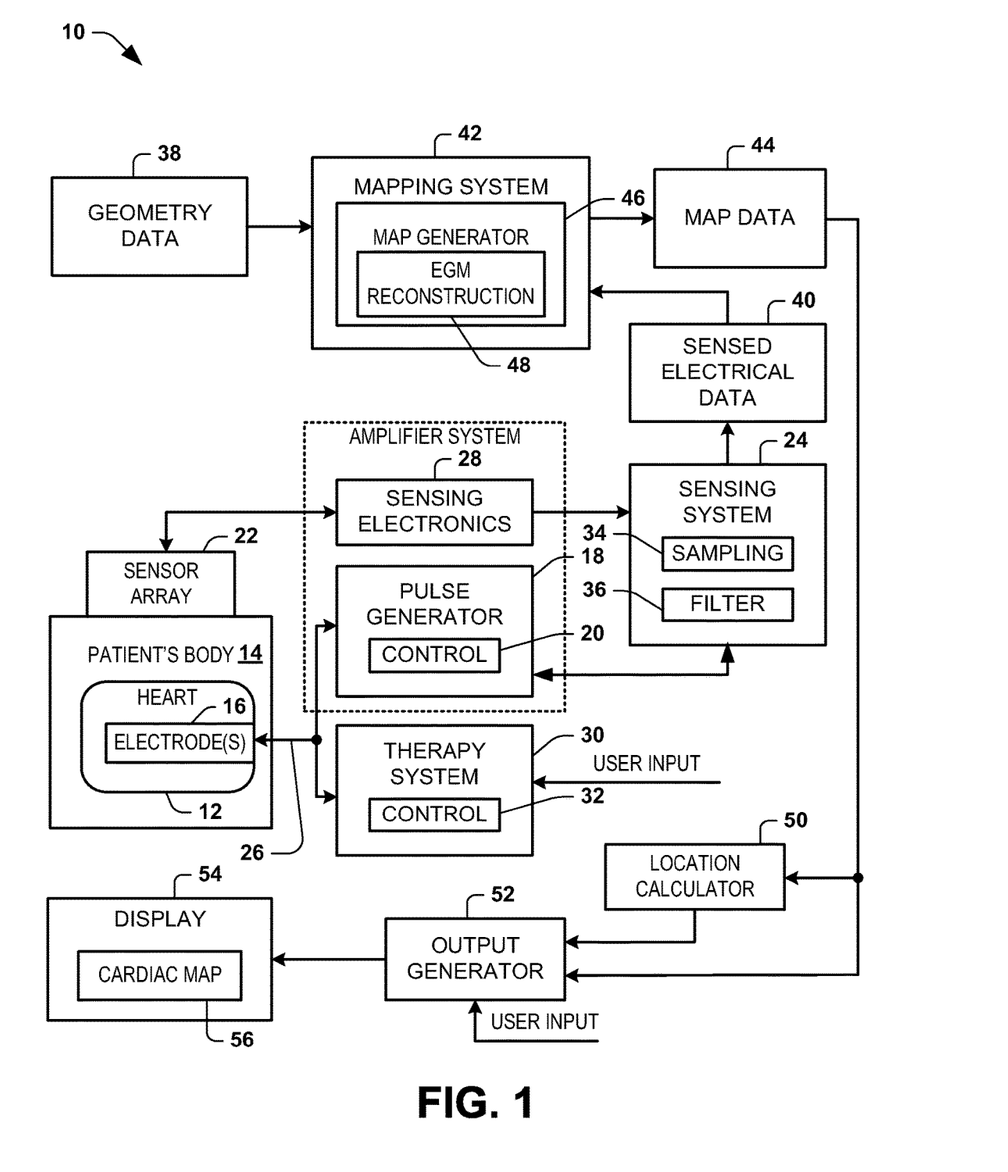
FIG. 1 depicts an example of a system for performing localization.

FIG. 1 depicts an example of a system 10 that can be utilized for electrocardiographic mapping of a patient's heart 12. The system 10 can perform localization of an object that is located on or within the heart 12 in substantially real time, such as part of a diagnostic and/or treatment procedure. For example, a catheter, such as a pacing catheter, having one or more electrodes 16 affixed thereto can be inserted into the body 14 and positioned to contact the patient's heart 12, endocardially or epicardially. Those skilled in the art will understand and appreciate various type and configurations of pacing catheters and electrophysiology (EP) catheters that can be utilized to position one or more electrodes 16 in the patient's body 14.

A pulse generator 18 can be configured to control application of an electrical signal delivered by the electrode 16. For instance, the pulse generator 18 includes a pulse control 20 that can be configured to activate the pulse generator to supply the pulse to the electrode via a conductive link 26 electrically connected between the electrode 16 and the pulse generator 18. As an example, an output of the pulse generator 18 can be electrically connected to a corresponding connector of an electrophysiology catheter, schematically corresponding to the link 26.

The pulse control 20 can control parameters for applying electrical signals to the heart 12 via the electrode 16. The control parameters can include amplitude, frequency content, pulse duration, pulse repetition rate, and pulse waveform shape. The pulse can be applied as a current pulse or a voltage pulse. Additionally, in an example where a catheter includes multiple electrodes 16, the pulse control 20 can control parameters for delivering location pulses selectively to different electrodes at different times such as via corresponding electrical links 26.

In some examples, the pulse generator 18 can be configured to provide the localization pulse as a subthreshold pulse. As used herein, the term "subthreshold" refers to a signal that is sufficiently large to be measureable via an arrangement of sensing electrodes above noise that is detected by the sensing electrodes, but that is not so large as to stimulate cardiac conduction (i.e., trigger an action potential to pace the heart). The pulse control 20 thus can control electrical parameters (e.g., pulse amplitude, pulse duration and frequency) of a subthreshold electrical signal that is applied by the electrode 16. As mentioned above, the subthreshold electrical signal can be supplied as a current or voltage pulse.

By way of further example, the control 20 can introduce the subthreshold electrical signal as a square current pulse having a predetermined subthreshold amplitude (e.g., about 0.5 mA) and a predetermined pulse duration (e.g., about 2 ms). The amplitude of this pulse can be approximately 25% of the current that is needed to pace the heart, thereby providing a wide safety margin; however, still producing an electrical field that is large enough to be measured on the surface of the body by a sensor array 22 of electrodes. Thus, the same array of body surface sensors in the array 22 detect both the cardiac electrical activity and the localization signal. The duration of the subthreshold electrical signal can be set according to a sampling interval of a sensing system 24 to ensure digitally sampling the resulting field at least once per sampling interval. For example, a pulse duration of about 2 ms can ensure sampling at least one for a sampling rate of about 1,000 samples/channel/sec. The duration (e.g., about 2 ms) of the subthreshold signal can be the same as normally used to pace the heart although at a subthreshold amplitude.

The pulse control 20 can also provide the subthreshold localization pulse such that the corresponding electric field detected by a sensor array 22 includes high frequency content that resides within the pass bandwidth of the sensing electronics 28 and the sensing system 24 to facilitate detection and signal processing. In this way, the same circuitry used to measure the electrical signals on the patient's body 14 for electrocardiographic (EC) mapping can be used efficiently for sensing the subthreshold localization pulse.

As another example, the pulse control 20 can control delivery of subthreshold pulses to electrodes residing on multiple catheters or pacing leads, such as for individual localization of each such catheter or lead. That is, the system 10 can localize one or more objects (e.g., electrodes) within the heart and concurrently provide an indication of the location of each such object (e.g., in an electrocardiographic map). This is conveniently applicable to an elongated structure (e.g., a catheter body) that may include multiple electrodes spaced along its length. Thus, by detecting the location of each of the electrodes relative to patient anatomy, the system 10 can use the individual electrodes to reconstruct a three-dimensional position and orientation of the elongated structure in relation to patient anatomy, as disclosed herein. The location at which the electrode (or electrodes) 16 is located can be varied, for example, in response to the physician advancing, retracting or otherwise adjusting the position of the electrode relative to the patient's anatomy. The location of the electrode(s) can be updated in substantially real time based on detecting localization pulses during such movement.

The control 20 can control parameters of the subthreshold electrical signal with various other combinations of current and duration. For example, a constant voltage pulse could be used instead of a constant current pulse. Additionally or alternatively, the shape of the subthreshold pulse does not have to be square, but could be any shape desired (e.g., sinusoidal, linear or non-linear ramp signals or the like).

As another example, the pulse control 20 can further control operation of the pulse generator 18 in multiple modes such as can include a localization mode and a therapy mode. During the localization mode, the pulse control 20 can control operating parameters of the pulse generator 18 to provide localization signal to the electrode 16. During the therapy mode, control 20 can control parameters of the electrical signal as to stimulate (e.g., pace) or apply other therapy (e.g., ablation) to the heart 12. Alternatively, during the therapy mode the control can disable the pulse generator 18 while therapy is delivered by another external therapy system 30. The therapy can include electrical stimulation as well as non-electrical types of therapy (e.g., chemical, temperature treatments and the like). The control 20 thus can coordinate its operation with delivery of a therapy.

The pulse control 20 can set the appropriate pulse parameters and operate in a selected one of the modes as noted above. The pulse control can set parameters automatically (e.g., the pulse control is programmed to control operation in one of the modes), manually (e.g., in response user input) or employ a combination of automatic and manual controls (e.g., semi-automatic). The pulse control 20, for example, can repeatedly alternate between the therapy mode and the localization mode to facilitate delivery of a desired therapy at a given location in the patient 14 as determined during the localization mode. For instance, sensor information (e.g., including electrode location, electrical parameters and the like) can be collected continuously including during the localization mode and supplied to the pulse generator 18 based on which the control 20 can selectively adjust parameters to adjust stimulation parameters for delivery of therapy during the therapy mode.

As yet another alternative example, the pulse generator 18 can be configured to operate only in the localization mode, such as by repeatedly providing a subthreshold localization signal over time, while electrical stimulation or another therapy is supplied by another system that is separate, such as the therapy system 30 disclosed herein. For instance, the pulse generator 18 and sensing electronics 28 can be electrically isolated from each other and integrated into an amplifier system. The therapy system 30 can thus be implemented as electronics, which are separate from the amplifier system, configured to deliver a therapy. As disclosed herein, the therapy can include electrical stimulation via supra threshold pulses to the electrode as well as other forms of therapy (e.g., ablation).

For example, the therapy system 30 can be implemented a cardiac stimulator for providing external pacing via one or more of the electrodes 16, such as any type of external pacemaker devices that can be found in an EP laboratory. The therapy system 30 can include a control 32 that is configured to control application of a supra threshold stimulation pulse to the electrodes 16 via the conductive link 26. Thus, the link 26 can be shared by the pulse generator 18 and therapy system 30 for applying pulses to each of the one or more electrodes 16. The control 32 can control electrical parameters of such pacing pulse in response to a user input to apply the pacing pulse (e.g., closing a switch) or such control can be automated according to a predefined pacing procedure. During pacing or other electrical stimulation therapy with a supra threshold pulse, the supra threshold pulse operates as the localization signal for performing localization of the stimulation therapy site.

By way of another example, the therapy system 30 can be configured to deliver a non-electrical therapy (e.g., ablation therapy, such as radio frequency ablation, laser ablation, cryotherapy or the like) to the patient's heart 12. In such an example, the electrode 16 can be fixedly mounted on the therapy delivery mechanism. The control 20 can coordinate delivery of a localization signal, such as a subthreshold pulse, with delivery of the therapy by the therapy system 30. Alternatively, the control can control application of the sub-threshold pulse according to a predetermined repetition rate such that the pulse closest in time to when the therapy is delivered can be identified as the therapy delivery site. In other examples, the system can interpolate between locations for the two localization signals closest in time to when the therapy is delivered. During delivery of the non-electrical therapy, the subthreshold pulse can operates as the localization signal for performing localization of the therapy delivery site. For example, the control 32 of the therapy system can provide a timing pulse utilized by the control 20 to provide a localization signal concurrently with the delivery of therapy. Alternatively or additionally, a user input employed to trigger delivery of the therapy can also be provided to the pulse generator to enable the control 20 to provide a localization signal concurrently with the delivery of therapy. An annotation (e.g., including a time of the ablation) can be made when ablation therapy is applied, which annotation can be displayed at the location determined to be the therapy site, as disclosed herein.

In the example of FIG. 1, the sensor array 22 can include one or more electrodes that can be utilized for recording patient electrical activity, including sensing the electric field corresponding to each localization signal. As one example, the sensor array 22 can correspond to an arrangement of body surface electrodes that are distributed over the patient's torso for measuring electrical activity associated with the patient's heart (e.g., as part of an electrocardiographic mapping procedure). The sensor array 22 can cover the entire torso of the patient 14 (e.g., having greater than about 200 electrodes circumscribing the patient's chest) or a selected zone thereof. Examples of a non-invasive sensor array that can be used is shown and described in International application No. PCT/US2009/063803, which was filed 10 Nov. 2009 and U.S. Provisional Patent Application No. 61/426,143, each of which application is incorporated herein by reference.

Additionally, in other examples, one or more sensors can be implemented via the electrode 16, such as can be part of an EP catheter. The EP catheter can be inserted into the patient's body 14 and into the heart 12 for sensing electrical activity endocardially and/or epicardially. As another alternative, the sensor array 22 can be an arrangement of electrodes disposed on other devices, such as patches, which can be placed on or near a patient's heart, endocardially and/or epicardially. These patches can be utilized during open chest and minimally invasive procedures to record electrical activity. Sensor electrodes on the EP catheter and/or patches thus can be utilized in combination with the sensor array 22 that resides outside of the patient's heart to monitor electrical activity of the patient's heart 12 from different perspectives concurrently.

In the example of FIG. 1, the sensor array 22 provides the sensed electrical information to the sensing electronics 28 such as forming part of an amplifier system. The sensing electronics 28 can include signal processing circuitry (e.g., filters, amplifiers, A/D converters and the like) for providing corresponding sensor signals corresponding to a representation of electrical activity detected by each of the sensors in the sensor array 22. Corresponding sensing electronics can operate on each channel separately, for example. There can be a plurality of channels—one for each sensing electrode. Thus, in some examples, the sensor array 22 can concurrently provide a plurality of sensor signals over each heart beat, which sensor signals can also include sensed localization signals and stimulation pulses as applied by the pulse generator 18 and/or therapy system 30.

The sensing electronics 28 provide corresponding digital signals to the sensing system 24. The sensing system 24 can be configured to control the data acquisition process for measuring electrical activity and providing sensed electrical data 40. The sensing system 24 can include a sampling control 34 to control and set a sample rate at which the sensed electrical data 40 is stored. The sample rate can be fixed or be variable. The sensing system 24 can also include a filter 36 that is configured to filter the sensed electrical signals from the sensing electronics 28. As an example, the sampling control 34 and the filter 36 can be implemented as computer executable instructions stored in memory and executed by a processor. For example, the filter characteristics can vary depending on the operating mode. Alternatively or additionally, the sensor signals can be processed along parallel filter paths that can apply different filter characteristics for each path such that each path can be utilized to generate sensed electrical data for different purposes.

As one example, the generated subthreshold pulses will not be correlated to the cardiac cycle, and therefore they will correspond to carrier signals on top of the sensed cardiac signals. Since the subthreshold pulses have high frequency content, the filter 36 can be implemented as a high-pass filter to extract sensed electrical signals resulting from the electric field produced by such subthreshold pulses (e.g., during localization). Alternatively or additionally, the frequency characteristics of the subthreshold pulse can be user-defined and, since known, the filter 36 can be specifically designed according to the user-defined subthreshold signal characteristics. The resulting filtered electrical information is thus stored as sensed electrical data 40 in memory. The sensed electrical data 40 which can be utilized in conjunction with the geometry data to determine the location of the electrode 16 that provided the subthreshold pulse. The sensing system 24 can employ another signal path that can be sampled without being high-pass filtered, which can correspond to electrical signal content (e.g., cardiac signals) outside of the high-pass filtered signals utilized for localization. Alternatively or additionally, the other signal content can be low-pass filtered to remove the effects of the localization pulse from the cardiac signals. The sensed electrical data 40 from these electrical signals can be processed to generate an electrocardiographic map corresponding to electrical activity of the heart, such as disclosed herein.

The sensed electrical data 40 can be acquired concurrently with the delivering electrical energy by the pulse generator 18 or therapy system 30. For example, the sensed electrical data 40 can include localization data to determine the location of the electrode 16. The localization data of the sensed electrical data 40 can correspond to electrical activity detected by the sensor array 22 in response to a subthreshold localization signal, in response to applying a supra threshold stimulation signal during therapy, or in response to both subthreshold and supra threshold signals applied to one or more of the electrodes 16. That is, localization data for each type of localization signal and therapy that is applied can be employed to determine location of the electrode 16 and, in turn, the location of the therapy delivery device that is within the patient's body 14. The sensed electrical data 40 can also be acquired in other modes, with or without localization signals, for electrocardiographic mapping, such as in the absence of application of therapy or application of subthreshold pulses.

The sensing system 24 can also employ a clock to append appropriate time stamps (e.g., a time index) to the data for indexing the temporal relationship between the respective sensed multi-channel electrical data 40 and the electrical signals being applied via the pulse generator to facilitate the evaluation and analysis thereof. The sensing system 24 can also automatically map the subthreshold pulse since the system 10 can track (e.g., it knows) exactly when the pulse is delivered.

The system 10 can also include a mapping system 42 programmed to combine the sensed electrical data 40 with geometry data 38 by applying an appropriate algorithm to provide corresponding map data 44. The map data 44 can represent electrical activity associated with the heart 12, such as corresponding to a plurality of reconstructed electrograms distributed over an envelope associated with a surface of the patient's heart 12. Examples of approaches that can be utilized to perform such mapping and reconstruction of electrical signals on a cardiac envelope, such as an epicardial or endocardial envelope, are disclosed in U.S. Pat. No. 6,772,004 and U.S. patent application Ser. No. 11/996,441, the disclosure of each of which is incorporated herein by reference in its entirety. The electrical activity can correspond to the electric field produced in response to the pulse generator 18 applying a subthreshold pulse within the patient's body (e.g., to the heart) during localization. Alternatively, or additionally, the sensed electrical activity can correspond to natural and/or paced electrical activity of the heart 12 itself, such as can be in response to a stimulation pulse applied by the pulse generator 18 or therapy system 30.

As a further example, the mapping system 42 can provide the map data 44 to represent reconstructed electrograms for an epicardial envelope of the patient's heart 12, such as when the data is acquired non-invasively via sensors distributed on the body surface or invasively with sensors distributed on or near the epicardial envelope. Alternatively, the map data 44 can be reconstructed for an endocardial surface of a patient's heart such as a segmented portion of the patient's heart (e.g., left and right ventricles). The reconstruction method and can vary depending upon the approach or approaches (e.g., a non-invasive or invasive sensor array 22) utilized for acquiring the sensed electrical data 40 and the form of the geometry data 38.

In the example of FIG. 1, the mapping system 42 includes a map generator 46 that produces the map data 44 based on the sensed electrical data 40 and geometry data 38. For the example, the map generator 46 can implement electrogram reconstruction 48 through an inverse algorithm programmed to process the electrical data 40 to produce corresponding electrogram data for each of a plurality of identifiable sites on a selected envelope associated with the patient's heart 12. The envelope can be implemented as an epicardial surface, an endocardial surface or other geometrical surface construct, which can be represented in the map data 44 as a two-dimensional or three-dimensional envelope.

As an example, the geometry data 38 may be in the form of graphical representation of the patient's torso, such as image data acquired for the patient. Such image processing can include extraction and segmentation of anatomical features, including one or more organs and other structures, from a digital image set. Additionally, a location for each of the electrodes in the sensor array 22 can be included in the geometry data 38, such as by acquiring the image while the electrodes are disposed on the patient and identifying the electrode locations in a coordinate system through appropriate image processing, including extraction and segmentation. The resulting segmented image data can be converted into a two-dimensional or three-dimensional graphical representation that includes the volume of interest for the patient.

Alternatively, the geometry data 38 can correspond to a mathematical model of the patient's torso that has been constructed based on image data for the patient's torso and regions of interest (e.g., the heart). Appropriate anatomical or other landmarks, including locations for the electrodes in the sensor array 22 can be identified in the geometry data 38 to facilitate registration of the electrical data 40 and performing the inverse method thereon. The identification of such landmarks can be done manually (e.g., by a person via image editing software) or automatically (e.g., via image processing techniques).

By way of further example, the geometry data 38 can be acquired using nearly any imaging modality based on which a corresponding representation can be constructed, such as described herein. Examples of imaging modalities include ultrasound, computed tomography (CT), 3D Rotational angiography (3DRA), magnetic resonance imaging (MRI), x-ray, positron emission tomography (PET), fluoroscopy and the like. Such imaging may be performed concurrently with recording the electrical activity that is utilized to generate the sensed electrical data 40 or the imaging can be performed separately (e.g., before or after the measurement data has been acquired).

Alternatively or additionally, the geometry data 38 can correspond to a generic or custom representation (e.g., a model) of the heart, which may not be the patient's own heart. In such a case, the sensed electrical data 40 can be mapped (e.g., via registration) to the representation of the organ according to identified anatomical landmarks. A manual, semi-automatic or automatic registration process can be employed in order to register the anatomical model with the signal acquisition system.

The system 10 also includes a location calculator 50 that is programmed to determine a location for one or more objects positioned in the patient 14. In the context of the example of FIG. 1, the location calculator 50 can ascertain a location where the localization electrical signal was applied (e.g., corresponding to the location of the electrode 16) based on an analysis of the map data 44, which includes reconstructed electrograms. This determination can be performed in real time or near real time so that it can provide intraoperative guidance for a physician. In some examples, the mapping of the location can be performed manually, such as in response to a user identifying the subthreshold pulse from a set of pulses over the surface of the heart (e.g., via a caliper user interface element to select a pulse or spike). Alternatively or additionally, the mapping of the pacing pulse can be implemented as an automated method based on computations performed by the location calculator 50 on the map data 44.

For example, where the map data 44 comprises reconstructed electrical signals for a plurality (e.g., hundreds or thousands) of discrete locations on a user-specified surface of the heart, the location calculator 50 can select a localized one of the mapped electrical signals as corresponding to an absolute location where the subthreshold signal was applied. As a further example, the map generator 46 can generate the map data 44 based on the geometry data 38 and sensed electrical data 40 that has been high-pass filtered for localization purposes (e.g., during a localization mode). The location calculator 50 can select a localized reconstructed electrical signal, corresponding to the electrode location, based on a comparison of the amplitudes of the high-pass filtered and mapped electrical signals. The location calculator can determine the location according to which high-pass filtered, reconstructed electrical signal has the greatest amplitude when the localization signal is applied. The location on the heart where such selected reconstructed electrical signal resides thus corresponds to the location of the electrode where the localization signal is applied. Thus, as the electrode is moved in the patient's body 14, the map data 44 can be updated so that the location calculator 50 can compute new location information commensurate with such movement.

Additionally, the location calculator 50 can be programmed to compute a localized reconstructed electrogram from a supra threshold pulse based on the activation time and amplitude of the reconstructed electrograms provided in the map data 44. For instance, the location calculator 50 can determine the localized electrode position where the supra threshold pulse is applied according to which reconstructed electrogram has an earliest activation time and a largest amplitude. In other examples, the location calculator 50 can be programmed to determine the localized electrode position where the supra threshold pulse is applied according to which reconstructed electrogram has either an earliest activation time or a largest amplitude. For example, the earliest activation time that is detected for a supra threshold (e.g., pacing) pulse, can identify an epicardial location corresponding to the location of the electrode. The localized maxima (e.g., largest amplitude) can correspond to an endocardial location where the pacing pulse was applied.

The system 10 also includes an output generator 52 that is configured to provide a graphical output to a display 54 based on the localization information determined by the location calculator 50, the map data 44 or a combination thereof. The display 54 thus can provide a visual representation of a cardiac map 56. The cardiac map 56 can include a graphical representation of the heart and, based on the location information, include a visual indicia at a corresponding location where the localization signal was applied. As one example, the visual indicia of the electrode location can be a graphical icon that is superimposed on a cardiac map 56 that has been generated based on map data 44. The map data can be generated as to include only localization information. Alternatively or additionally, the map data 44 can include reconstructed cardiac electrical activity for the heart (e.g., natural and/or paced), and the visual indicia of location can be superimposed on a cardiac map corresponding to such reconstructed cardiac electrical activity. Regardless of which type or types of electrical map data is being displayed in the cardiac map 56, the location calculator 50 can update the visual indicia in substantially real time to reflect the current location of the electrode 16.

In some examples, the output generator 52 can be programmed to provide different forms of localization indicators for different types of detected signals. For instance, the output generator 52 can produce a first type of visual indicator to reflect a moveable location corresponding to an electrode or catheter that can be moved relative to the heart. In this way the first type of visual indicator provided in the cardiac map reflects movement of the electrodes relative to the heart. This type thus can provide real time feedback to the user such as to facilitate pacing or delivery of other therapy.

The output generator 52 can also produce a second type of visual indicator that can remain fixed in the cardiac map regardless of movement of the electrodes and changes in sensed electrical activity. The second type of visual indicator can correspond to a pacing site at which a supra threshold pacing pulse was applied. In this way, the output generator can maintain a convenient record of each pacing site that is readily available to the user via the display 54. The location information for this second type of visual indicator can also be automatically registered into a coordinate system of another image modality based on reference to common fiducial markers in each imaging modality and the geometry data 38. For example, an indication of a therapy delivery location can be rendered on a display of another imaging modality, such as fluoroscopy, x-ray, 2-D or 3-D cardiac echo, to provide a visual record in such image of the location where therapy was applied (e.g., a pacing site or ablation site).

The output generator 52 can also include a mechanism (e.g., a graphical user interface) to enable a user to select and remove a user-selected second type of visual indicator for a pacing location, such as if the user determines that the pacing site does not provide desired results. Additionally or alternatively, the output generator 52 can include a graphical user interface that is programmed to insert a pacing site visual indicator on the cardiac map 56 automatically in response to detecting that a pacing pulse is applied to one or more electrodes 16. The detection can be in response to a user input that is supplied to the pulse generator 18 or 30, detecting a pacing pulse in the map data 44 or a combination thereof. The output system can also be programmed to control the type of information presented in the cardiac map in response to a user input via a graphical user interface (e.g., a potential map, an activation map, a depolarization map, a synchronization map or the like).

The location for each of the fixed location and moveable location indicators can be stored in memory along with the map data 44 for later review, for example. Alternatively, the location information for one or both types can be recomputed based on map data 44 as disclosed herein.

Figure 2:
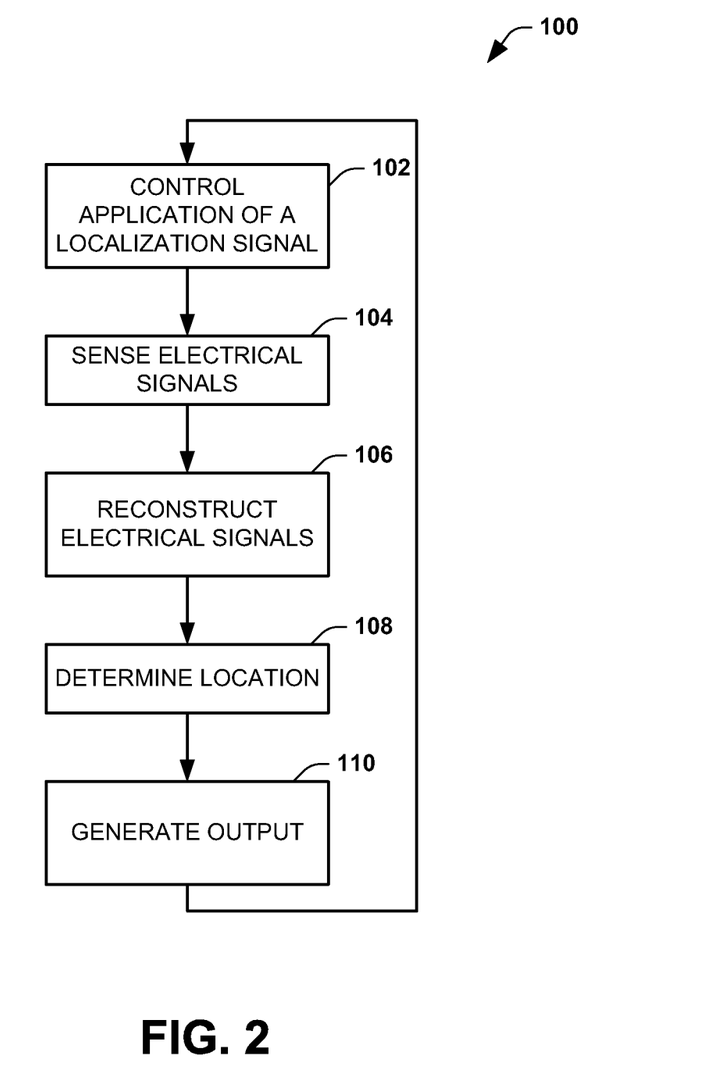
FIG. 2 depicts an example of a method for performing localization.

In view of the foregoing structural and functional features described above, example methods will be better appreciated with reference to FIG. 2. While, for purposes of simplicity of explanation, the example method of FIG. 2 is shown and described as executing serially, it is to be understood and appreciated that the present examples are not limited by the illustrated order, as some actions could in other examples occur in different orders and/or concurrently from that shown and described herein. The method can be implemented as computer readable instructions, such as can be stored in a non-transitory computer readable medium, such as a volatile or non-volatile memory device. The instructions in the medium may further be executed by a processing unit.

FIG. 2 is flow diagram depicting an example of a method 100 that can be employed to localize an object in the patient as disclosed herein. For example, the method 100 can be performed in the context of performing a low or minimally invasive procedure on the patient's heart, such as with a catheter or pacing lead that includes one or more electrodes (e.g., electrode 16 of FIG. 1). As an example, the catheterization procedure can be performed to provide for cardiac resynchronization therapy (CRT), cardiac ablation or other similar types of procedures. During such procedure, the method 100 can be implemented to localize the catheter. The method 100 can also be utilized to localize one or more pacing leads, such as from a CRT device or a pacemaker.

The method 100 begins at 102 in which application of a localization is controlled. For instance, the catheter carrying the electrode can be advanced to the patient's heart and a subthreshold electrical signal can be applied (e.g., by the pulse generator 18 of FIG. 1) to produce a corresponding electric field within the patient's body. The subthreshold signal can be generated as a current pulse or voltage pulse having a controlled duration and frequency, such as disclosed herein. Alternatively, the localization signal can be implemented as a supra threshold electrical signal with an amplitude sufficient to stimulate a conductive pathway in the patient. The control can be automated or be provided in response to a user input.

At 104, electrical signals can be sensed. For example, an arrangement of sensors (e.g., the sensor array 22) can be distributed across the patient's torso to noninvasively sense electrical potentials on the body surface, including electrical signals corresponding to the subthreshold electrical signal applied at 102. The sensed electrical signal can undergo analog and digital processing. For example, the signals can be filtered (e.g., by high pass filters) to pass frequency content corresponding to an electrical field caused by the localization signal as well as content corresponding to natural or paced electrical activity of the heart. The processed signals can be stored in memory as sensed electrical data (e.g., data 40 of FIG. 1). Because the sensors can concurrently detect body surface electrical potentials across the entire body surface or a selected portion thereof, the method and system disclosed herein can also localize the electrode to an absolute position in three-dimensional space as well as be utilized to display other cardiac electrical activity concurrently.

At 106, the sensed electrical signals are utilized to reconstruct electrical signal onto a cardiac envelope (e.g., by the mapping system 42 of FIG. 1), such as can be an endocardial surface, an epicardial surface or other cardiac envelope. For example, the mapping at 106 can be implemented via an algorithm that translates the noninvasively measured body surface electrical potentials to the heart electrical activity data based on geometry data and the sensed electrical data.

At 108, the method 100 includes determining a location where the subthreshold pulse was applied based on analysis of the reconstructed electrical signals provided at 106. As one example, the location can be determined by selecting a localized mapping signal, corresponding to an absolute location where the localization signal was applied. Such localized mapping signal can be selected from a plurality of reconstructed electrical signals that have been mapped onto the surface of the heart. The localized mapping signal for the electrode location can be the signal having the largest amplitude and have frequency characteristics corresponding to the frequency of the subthreshold pulse applied at 102. Alternatively, the localized mapping signal can correspond to the location of a supra threshold pulse that is selected from the reconstructed electrograms based on activation time and amplitude.

At 110, an output can be generated (e.g., by the output generator 52 of FIG. 1). The output can be provided as including a graphical display (e.g., an image representation) of the heart that includes a visual indicator at the location where the localization signal was applied to the heart by the electrode (e.g., corresponding to localized mapping signal). The method 100 can be repeated intraoperatively to help guide the catheter relative to the patient's heart, and as the electrode moves relative to the heart the method can update the output in substantially real time to reflect a current location of the electrode. Additional electrical activity of the heart (natural and/or pacing) can also be displayed concurrently with the location of the electrode superimposed thereon to further assist the user. As an example, the localization method can be used for catheter localization in conjunction with applying a therapy (e.g., pacing and/or ablation) for treatment of any type of arrhythmia (focal or re-entrant arrhythmias) as well as for sinus rhythm disorders.

Figure 3:
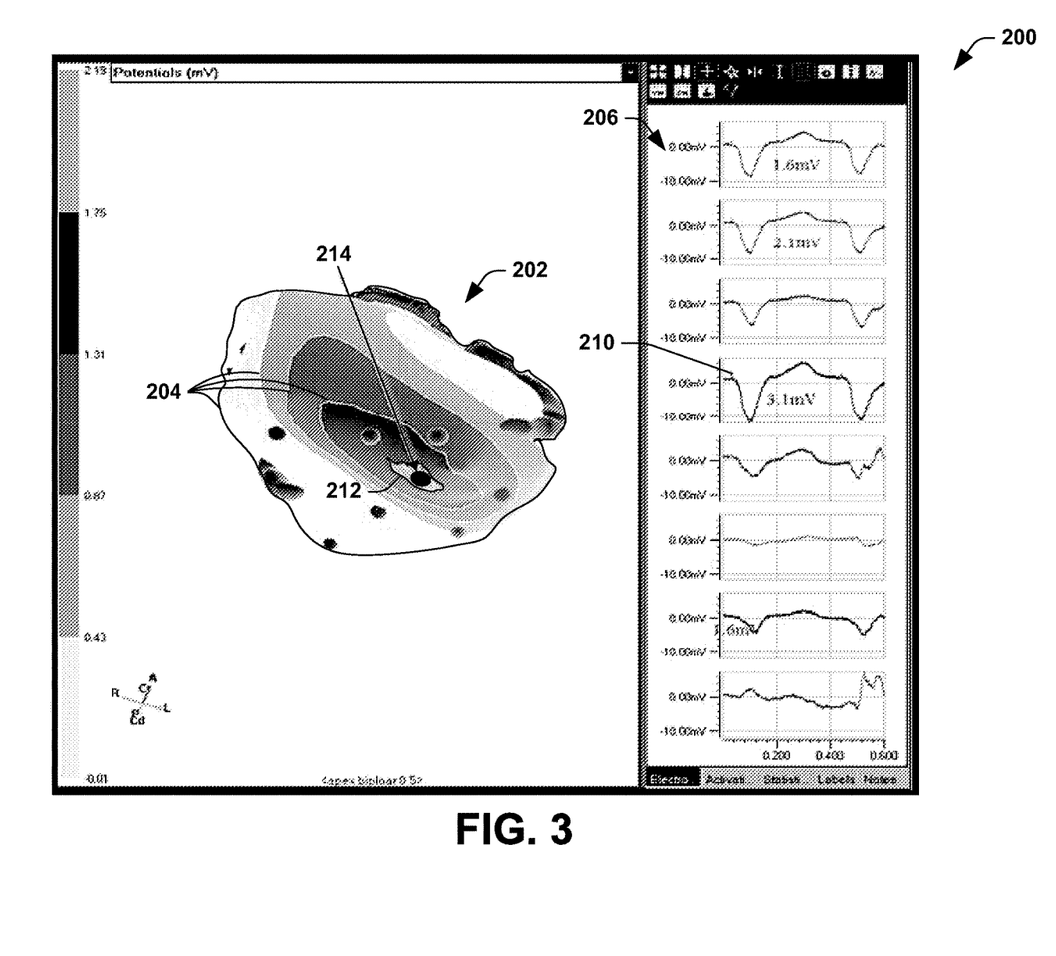
FIG. 3 depicts a screen shot demonstrating an example of graphical user interface that includes an electrocardiographic map and a location indicator that can be generated according to systems and methods disclosed herein.

FIG. 3 depicts an example of a display 200 (e.g., a graphical user interface) that can be generated by systems and methods disclosed herein. In the example of FIG. 3, the display 200 includes a graphical representation of a heart 202 on which a potential map 204 has been displayed corresponding to electrical potentials at a selected time. The time can be user selected via a graphical user interface or it can be automatically selected (e.g., via signal processing techniques to ascertain a time interval containing such pulses). For instance, the time can correspond to a period of time when a localization pulse is applied to the heart. The display also includes plots 206 of heart electrical activity signals (e.g., electrical traces of electrical potentials mapped to the heart by the mapping system 42 of FIG. 1) corresponding to the electrical field produced by the subthreshold pulse.

In the example of FIG. 3, the electrical field corresponds to a localization signal that was provided as a subthreshold pulse, which is superimposed (e.g., by adding signals) on the signals produced by electrical activity of the heart. Additionally, signal processing can be performed to isolate the electrical field of the subthreshold pulse from the cardiac electrical activity and provide a representation of such signals in the display 200. The display may also include a cine mode that can be activated, in response to a user input. In the cine mode, the potential map 204 in the display 200 can vary as a function of time, which can proceed in a forward, reverse, loop or other user-selected temporal manner The subthreshold pulses, corresponding to reconstructed electrograms in the graphical plots 206, are demonstrated in the display 200 on the first, second and fourth traces on the right-hand side of the display. In the example, of FIG. 3, the reconstructed electrogram having the largest spike is indicated at 210. Each of the reconstructed electrical localization pulses can be identified from the electrograms plots 206 by the user via a user interface or from the underlying reconstructed electrogram data by automated detection methods. A central area of the map, indicated as region 212, represents the highest potential of the electric signals, corresponding to the localized maxima 210, which can be identified by the location calculator as corresponding to the location of the catheter (e.g., via an electrode on the catheter) that is generating this localization field. A visual indicator 214 thus can be rendered in the display at a centroid of the identified region 212 to identify a location on the surface of the heart where the subthreshold localization signal was applied. The display 200 can also include GUI features and scales to facilitate interpretation of the map data that is displayed as well to enable re-orientation of the heart in a given coordinate system.

Figure 4:
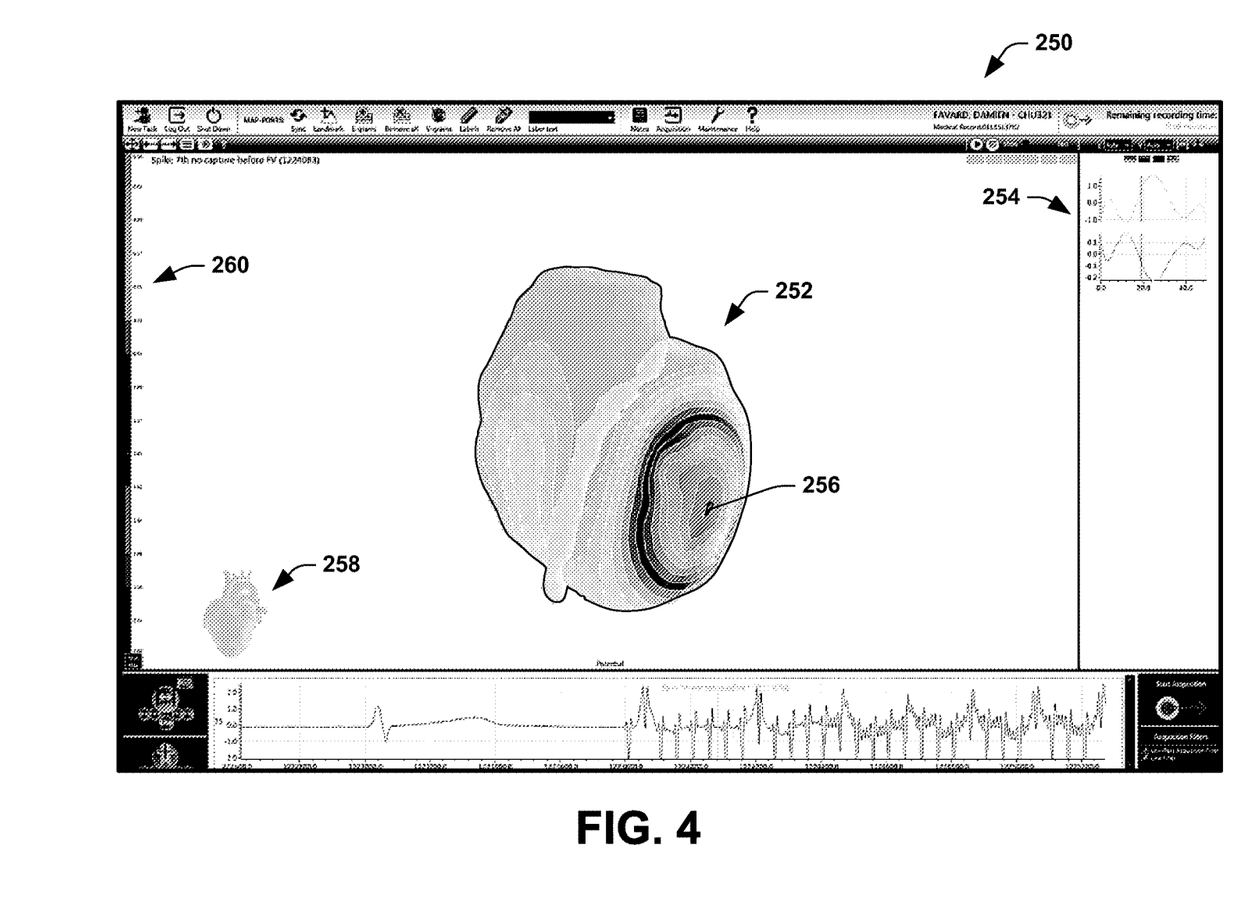
FIG. 4 depicts a screen shot demonstrating another example of graphical user interface that includes an electrocardiographic map and a location indicator that can be generated according to systems and methods disclosed herein.

FIG. 4 depicts another example of a display 250 (e.g., a graphical user interface) that can be generated by systems and methods disclosed herein. In the example of FIG. 4, the display 250 includes a graphical representation of a heart 252 on which a potential map has been displayed corresponding to reconstructed electrical signals at a selected time. In the example of FIG. 4, the reconstructed electrical signals are based on a supra threshold stimulation signal (e.g., a pacing signal) that is applied via an electrode. The display 250 also includes plots 254 of reconstructed electrical signals that are utilized to generate the map on the heart 252. A region having the highest amplitude and earliest activation time is identified at 256 to represent the location of the electrode at which the supra threshold localization signal is applied.

The display also includes a heart GUI element 258 that represents an orientation of the heart map 252. A user thus can employ a pointing device (e.g., mouse) or other user input device to rotate the heart GUI element to rotate the heart map 252 accordingly. The display also includes a scale 260 that can provide an indication of the color codes presented on the heart map 252, such as can correspond to activation time, for example.

Figure 5:
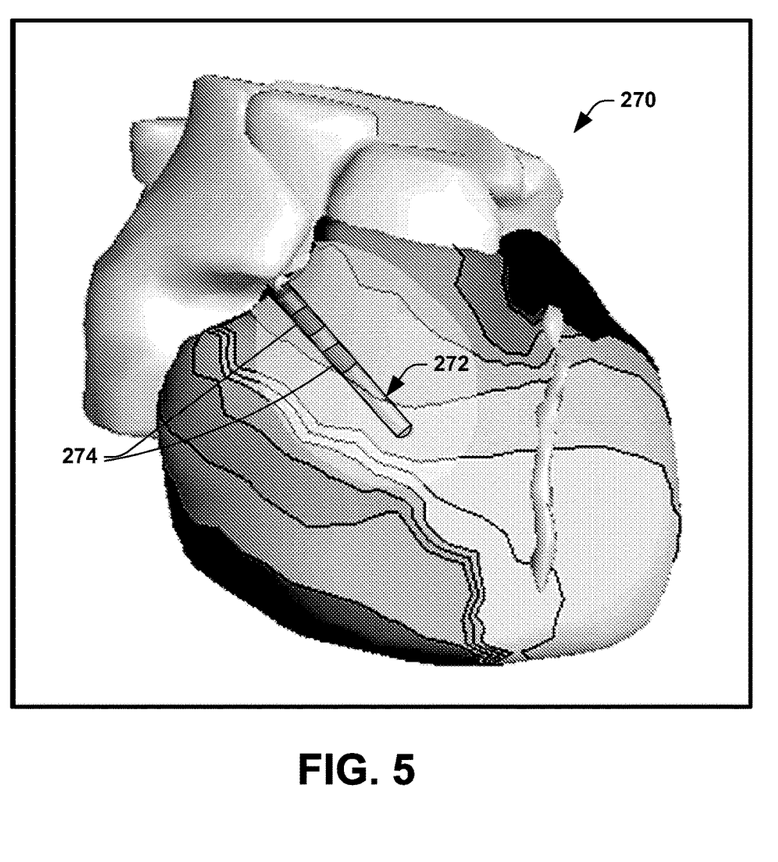
FIG. 5 depicts an example of electrocardiographic map that can be generated demonstrating a representation of an object on an electrocardiographic map.

FIG. 5 demonstrates an example EC map 270 of a heart in which a graphical representation of a cardiac catheter 272 is superimposed on an image of the heart. The example catheter is shown to include two electrodes 274, although it will be understood that the catheter that is shown can include any number of electrodes such as can be commensurate with an actual catheter design being used by a user during delivery of a therapy. For example, a user can identify the type and configuration of catheter (e.g., by manufacturer and model number), such as can be selected from a list provided via a graphical user interface. The system can thus graphically present the selected type and configuration of catheter in the display at a position determined based on the approach disclosed herein. The location of the catheter 272 can be determined and presented on the cardiac map 270 by determining location of one or both electrodes 274 in response to in supplying localization signals (subthreshold and/or supra threshold electrical signals) to electrodes of an actual catheter that is inserted into the patient's body. Movement of the catheter relative to the heart can similarly be tracked and displayed on the map 270.

Figure 6A:
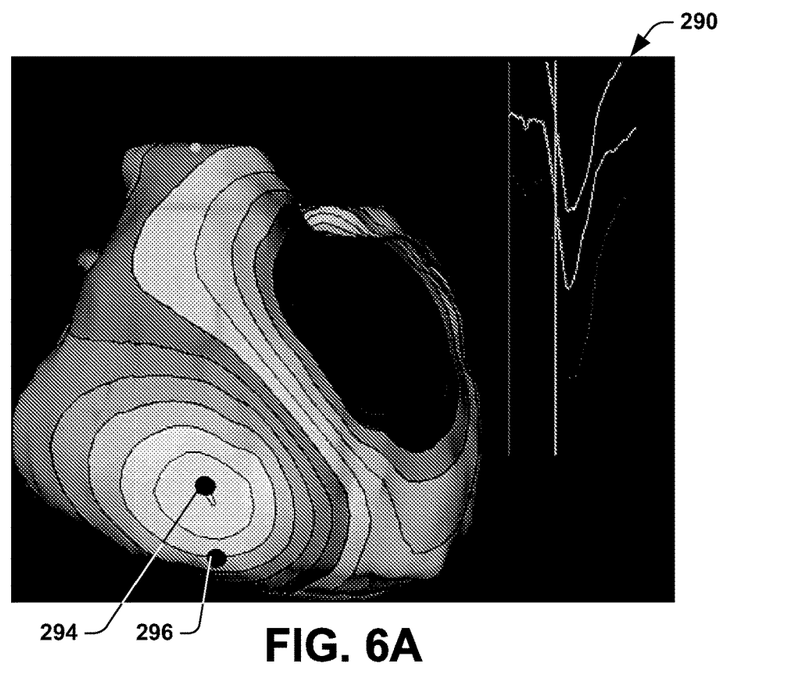
FIGS. 6A and 6B depict examples of electrocardiographic maps demonstrating both endocardial and epicardial location indicators that can be generated according to systems and methods disclosed herein.
Figure 6B:
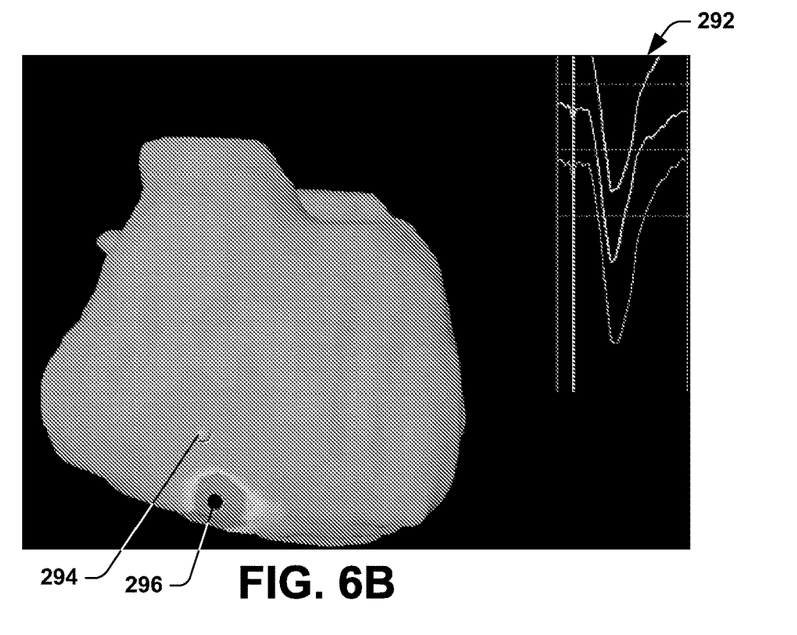

FIGS. 6A and 6B depict examples of electrocardiographic maps 290 and 292 demonstrating localized anatomical positions 294 and 296, respectively, determined in response to application of a given supra threshold localization (e.g., pacing) pulse. The corresponding location 294 corresponds to a projection on the endocardium of the epicardial activation that is computed from reconstructed electrograms based on their respective activation times. Thus as shown in FIG. 6A, the map depicts an activation map for the heart and the location 294 corresponds to a center of earliest activation. The other location 296 is presented in FIG. 6A for comparison purposes. The location 296, as shown in FIG. 6B, corresponds to an endocardial location that is determined based on a localized amplitude maxima computed from reconstructed electrograms such as demonstrated in FIG. 6B. FIGS. 6A and 6B demonstrate electrograms from which the locations 294 and 296 have been computed along with a timing caliper that shows which part of the signal is utilized to generate the respective maps 290 and 292. For instance, the activation map 290 is generated based on the activation time for conduction of cardiac tissue. The potential map 292 shows supra threshold pulses that are utilized to generate the map and thereby determine a local maxima that identifies a corresponding endocardial location corresponding to the pacing site.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware, such as shown and described with respect to the computer system of FIG. 7. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Figure 7:
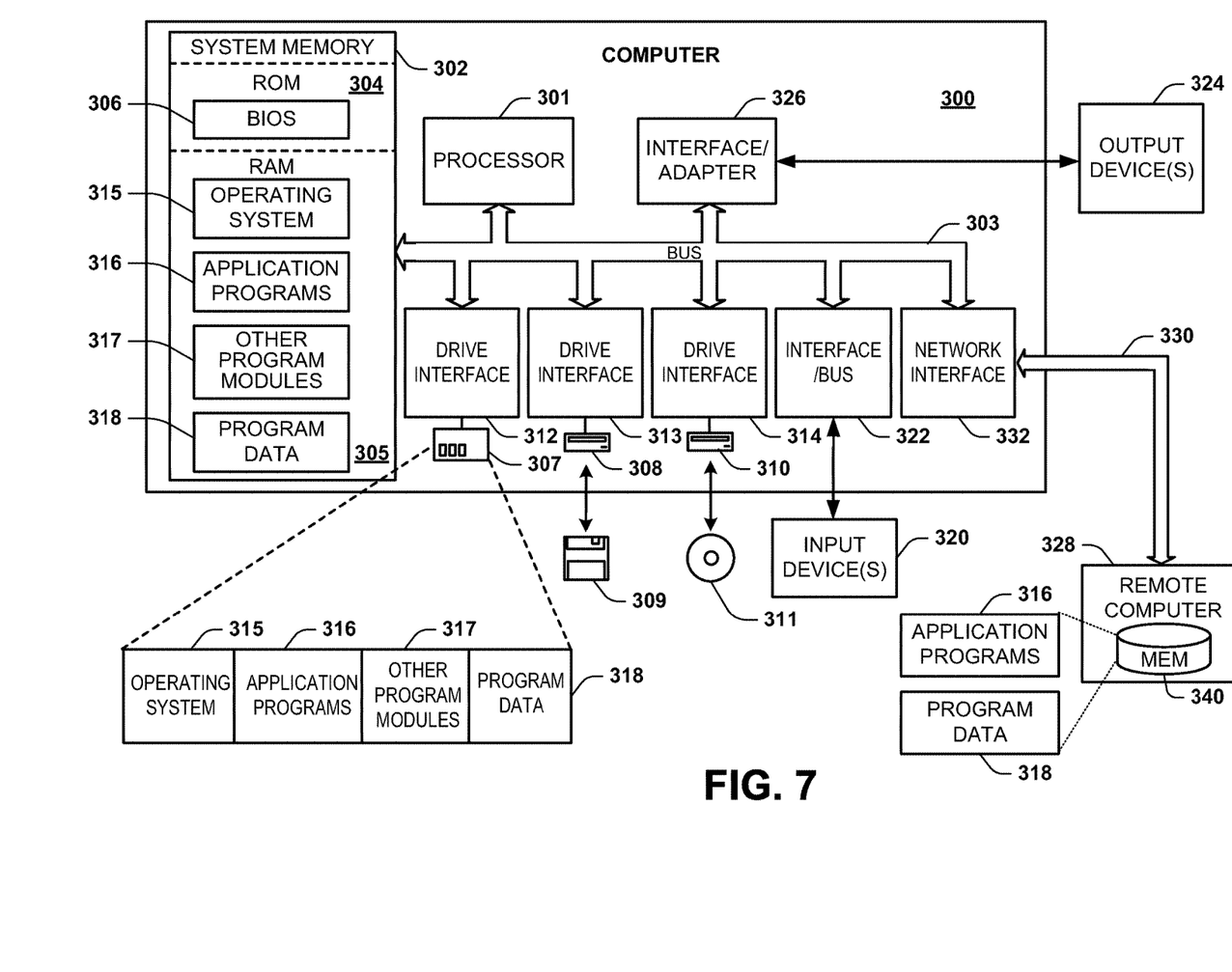
FIG. 7 depicts an example computing environment that can be used to perform methods according to an embodiment of the invention.

In this regard, FIG. 7 illustrates one example of a computer system 300 that can be employed to execute one or more embodiments of the invention, such as including acquisition and processing of sensor data, processing of image data, as well as analysis of transformed sensor data and image data associated with the analysis of cardiac electrical activity. Computer system 300 can be implemented on one or more general purpose networked computer systems, embedded computer systems, routers, switches, server devices, client devices, various intermediate devices/nodes or stand alone computer systems. Additionally, computer system 300 can be implemented on various mobile clients such as, for example, a personal digital assistant (PDA), laptop computer, pager, and the like, provided it includes sufficient processing capabilities.

Computer system 300 includes processing unit 301, system memory 302, and system bus 303 that couples various system components, including the system memory, to processing unit 301. Dual microprocessors and other multiprocessor architectures also can be used as processing unit 301. System bus 303 may be any of several types of bus structure including a memory bus or memory controller, a peripheral bus, and a local bus using any of a variety of bus architectures. System memory 302 includes read only memory (ROM) 304 and random access memory (RAM) 305. A basic input/output system (BIOS) 306 can reside in ROM 304 containing the basic routines that help to transfer information among elements within computer system 300.

Computer system 300 can include a hard disk drive 307, magnetic disk drive 308, e.g., to read from or write to removable disk 309, and an optical disk drive 310, e.g., for reading CD-ROM disk 311 or to read from or write to other optical media. Hard disk drive 307, magnetic disk drive 308, and optical disk drive 310 are connected to system bus 303 by a hard disk drive interface 312, a magnetic disk drive interface 313, and an optical drive interface 314, respectively. The drives and their associated computer-readable media provide nonvolatile storage of data, data structures, and computer-executable instructions for computer system 300. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of the present invention.

A number of program modules may be stored in drives and RAM 305, including operating system 315, one or more application programs 316, other program modules 317, and program data 318. The application programs 316, for example, and program data can include functions and methods programmed to acquire, process and display electrical data from one or more sensors, such as shown and described herein. The application programs 316, for example, can include functions and methods programmed to perform the functions of the sensing system 24, the mapping system 42, the location calculator 50 and output generator 52 of FIG. 1. The sensed electrical data 40, geometry data 38, and the map data 44 of FIG. 1 can be stored, for example, in memory 302 and 307. Additionally, the application programs and program data can include functions and methods programmed to perform the method of FIG. 2, and to generate the outputs as disclosed with respect to FIGS. 3-6.

A user may enter commands and information into computer system 300 through one or more input devices 320, such as a pointing device (e.g., a mouse, touch screen), keyboard, microphone, joystick, game pad, scanner, and the like. For instance, the user can employ input device 320 to edit or modify a domain model. These and other input devices 320 are often connected to processing unit 301 through a corresponding port interface 322 that is coupled to the system bus, but may be connected by other interfaces, such as a parallel port, serial port, or universal serial bus (USB). One or more output devices 324 (e.g., display, a monitor, printer, projector, or other type of displaying device) is also connected to system bus 303 via interface 326, such as a video adapter.

Computer system 300 may operate in a networked environment using logical connections to one or more remote computers, such as remote computer 328. Remote computer 328 may be a workstation, computer system, router, peer device, or other common network node, and typically includes many or all the elements described relative to computer system 300. The logical connections, schematically indicated at 330, can include a local area network (LAN) and a wide area network (WAN).

When used in a LAN networking environment, computer system 300 can be connected to the local network through a network interface or adapter 332. When used in a WAN networking environment, computer system 300 can include a modem, or can be connected to a communications server on the LAN. The modem, which may be internal or external, can be connected to system bus 303 via an appropriate port interface. In a networked environment, application programs 316 or program data 318 depicted relative to computer system 300, or portions thereof, may be stored in a remote memory storage device 340.

What have been described above are examples. It is, of course, not possible to describe every conceivable combination of components or methodologies, but one of ordinary skill in the art will recognize that many further combinations and permutations are possible. Accordingly, the invention is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A system to localize an object in a patient's body, the system comprising:
   at least one electrode fixed to the object in the patient's body;
   a pulse generator configured to generate a localization signal comprising a subthreshold electrical signal and provide the localization signal to the at least one electrode, the subthreshold electrical signal having energy insufficient to stimulate electrical conduction in tissue of the patient's body;
   a sensor array configured to detect an electrical field produced in response to the localization signal and provide respective sensor signals; and
   a processor configured to:
      retrieve geometry data stored in memory, the geometry data representing a geometric relationship between patient anatomy and the sensor array;
      reconstruct electrical signals based on the respective sensor signals and the geometry data; and
      determine an absolute location where the localization signal was applied based on comparing amplitude and frequency characteristics of each of the reconstructed electrical signals with respect to the localization signal.

2. The system of claim 1, wherein the localization signal further comprising a supra threshold electrical signal, the supra threshold electrical signal having energy sufficient to stimulate electrical conduction in tissue of the patient's body.

3. The system of claim 1, further comprising an output generator configured to provide output data representing a graphical display of a heart of a patient that includes an indicator at the absolute location where the localization signal was applied.

4. The system of claim 3,
wherein the object is one of a catheter or pacing lead; and
wherein the output generator is configured to:
generate a graphical display of the heart of the patient as an electrocardiographic map based on the reconstructed electrical signals;
superimpose a first visual indicator on a location of the electrocardiographic map to indicate the absolute location where the localization signal was applied; and
superimpose a second visual indicator on the electrocardiographic map to reflect movement of the catheter or the pacing lead relative to the heart of the patient.

5. The system of claim 1, further comprising a cardiac stimulation system configured to deliver therapy to a therapy site in the patient's body corresponding to a location on a heart of the patient's body, the at least one electrode being affixed to a selectively moveable element of the cardiac stimulation system, at least one of the pulse generator and the cardiac stimulation system being configured to provide the localization signal to the at least one electrode.

6. The system of claim 5, further comprising an output generator configured to provide output data representing a graphical display of the heart, the graphical display of the heart including an indicator at the absolute location where the localization signal was applied, the indicator being presented at a fixed location in the graphical display of the heart to identify the therapy site.

7. The system of claim 5, further comprising an output generator configured to provide output data representing a graphical display of the heart, the graphical display of the heart including an indicator at the absolute location where the localization signal was applied, the indicator being moveable in the graphical display of the heart commensurate with a current location of the selectively moveable element of the cardiac stimulation system.

8. The system of claim 5, wherein the cardiac stimulation system comprises one of an ablation therapy system and a pacing therapy system.

9. The system of claim 1, further comprising a high-pass filter configured to filter the respective sensor signals to extract signal content corresponding to the electrical field produced in response to the localization signal.

10. The system of claim 1, wherein the pulse generator is configured to supply the localization signal to include a combination of the subthreshold electrical signal and a supra threshold signal applied at different times, the supra threshold electrical signal having energy sufficient to stimulate electrical conduction in tissue of the patient's body.

11. The system of claim 1, further comprising a cardiac stimulation system configured to control delivery of therapy to a therapy site based on the determined absolute location.

12. The system of claim 11, wherein the cardiac stimulation system comprises one of an ablation therapy system and a pacing therapy system.

* * * * *